United States Patent
Ueno

(10) Patent No.: US 7,063,857 B1
(45) Date of Patent: Jun. 20, 2006

(54) USE OF MACROLIDE COMPOUNDS FOR THE TREATMENT OF DRY EYE

(75) Inventor: Ryuji Ueno, Montgomery, MD (US)

(73) Assignee: Sucampo AG, Zug (CH)

( * ) Notice: Subject to any disclaimer, the term of this patent is extended or adjusted under 35 U.S.C. 154(b) by 0 days.

(21) Appl. No.: 09/926,411

(22) PCT Filed: Apr. 26, 2000

(86) PCT No.: PCT/JP00/02756

§ 371 (c)(1),
(2), (4) Date: Oct. 29, 2001

(87) PCT Pub. No.: WO00/66122

PCT Pub. Date: Nov. 9, 2000

Related U.S. Application Data

(60) Provisional application No. 60/132,009, filed on Apr. 30, 1999.

(51) Int. Cl.
- A61F 2/02 (2006.01)
- A61K 31/74 (2006.01)
- A61K 9/20 (2006.01)
- A61K 9/48 (2006.01)

(52) U.S. Cl. ............... 424/423; 424/78.04; 424/451; 424/464

(58) Field of Classification Search ............ 424/423, 424/78.04, 451, 464
See application file for complete search history.

(56) References Cited

U.S. PATENT DOCUMENTS

| | | |
|---|---|---|
| 5,457,182 A | 10/1995 | Wiederrecht et al. |
| 5,770,607 A | 6/1998 | Honbo et al. |
| 5,932,243 A | 8/1999 | Fricker et al. |
| 5,952,371 A | 9/1999 | Baker et al. |
| 6,004,565 A | 12/1999 | Chiba et al. |
| 6,376,517 B1 | 4/2002 | Ross et al. |
| 6,489,335 B1 | 12/2002 | Peyman |

FOREIGN PATENT DOCUMENTS

| | | |
|---|---|---|
| EP | 0 184 162 A2 | 6/1986 |
| EP | 0 240 773 A1 | 10/1987 |
| EP | 0 323 042 A1 | 7/1989 |
| EP | 0 406 791 A2 | 1/1991 |
| EP | 0 423 714 A2 | 4/1991 |
| EP | 0 427 680 A1 | 5/1991 |
| EP | 0 465 426 A1 | 1/1992 |
| EP | 0 480 523 A1 | 4/1992 |
| EP | 0 532 088 A1 | 3/1993 |
| EP | 0 532 089 A1 | 3/1993 |
| EP | 0 532 862 | 3/1993 |
| EP | 0 569 337 A1 | 11/1993 |
| EP | 0 626 385 A1 | 11/1994 |
| GB | 2 278 780 | 12/1994 |
| WO | WO 89/05303 | 6/1989 |
| WO | WO 91/13889 | 9/1991 |
| WO | WO 91/19495 | 12/1991 |
| WO | WO 93/05058 | 3/1993 |
| WO | WO 93/05059 | 3/1993 |
| WO | WO 94/09010 | 4/1994 |
| WO | WO 95/16691 | 6/1995 |
| WO | 96 31514 | 10/1996 |
| WO | WO 96/31514 | 10/1996 |
| WO | 97 25977 | 7/1997 |
| WO | WO 98/36747 | 8/1998 |
| WO | 99 55332 | 11/1999 |
| WO | 00 09109 | 2/2000 |

OTHER PUBLICATIONS

Web MD health Guide, "Keratoconjunctivitis, Vernal", pp. 1–3, NIH/National Eye Institute, Mar. 18, 2003.*
Yamada, M., et al., *Folia Ophthalmol. Jpn.*, vol. 43, pp. 1289–1293 (1992).
Jihong Yang et al.: "Sjogren's syndrome in mice carrying the Iprcg gene and the therapeutic efficacy of an immunasuppressive agent FK506" Pathol. Int., pp. 133–140 Feb. 1999.
K. Tsubota: "New approaches to dry–eye therapy" International Ophthalmology Clinics, US, Little, Brown, Boston, vol. 34, No. 1, pp. 115–128 1994.
H. Iwamoto et al.: "Inhibitory effects of FK506 on development of experimental allergic/immune–mediated blepharoconjunctivitis in Lewis rats by systemic but not by topical administration." Graefes Archive for Clinical and Experimental Ophthalmology, pp. 407–417 May 1999.
A. Tsujikawa et al.: "Tacrolimus (FK506) attenuates leukocyte accumulation after transient retinal ischemia" Stroke, US, American Heart Association, Dallas TX, vol. 29, No. 7, pp. 1431–1438 1998.
K.F. Tabbara et al.: "Dry eye syndrome" Drugs of Today/Medicamentos De Actualidad, ES, J.R. Prous SS.A International Publishers, vol. 34, No. 5, pp. 447–453 1998.

* cited by examiner

*Primary Examiner*—Carlos A. Azpuru
(74) *Attorney, Agent, or Firm*—Oblon, Spivak, McClelland, Maier & Neustadt, P.C.

(57) ABSTRACT

The present invention provides an agent for treating a dry eye, which contains a macrolide compound such as FK506.

9 Claims, No Drawings

USE OF MACROLIDE COMPOUNDS FOR THE TREATMENT OF DRY EYE

This application is a 371 application of PCT/JP00/02756, which was filed on Apr. 26, 2000, which claims priority to U.S. Provisional Patent Application No. 60/137,009, which was filed on Apr. 30, 1999, both of which are incorporated herein by reference in their entireties.

TECHNICAL FIELD

The present invention relates to an agent for treating a dry eye.

BACKGROUND ART

One of the symptoms of ophthalmic diseases drawing much attention these days is dry eye. The dry eye is defined to mean a condition wherein lacrimal fluid is less in amount or abnormal in quality, with or without the presence of corneal and conjunctival lesion (Yamada, M. et al., Folia Ophthalmol. Jpn., 43, 1289–1293 (1992)). Specific symptoms include dry eye observed in hypolacrimation, alacrima, xerophthalmia, Sjögren syndrome, keratoconjunctivitis sicca, Stevens-Johnson syndrome, ocular pemphigoid, marginal blepharitis, diabetes and the like, dry eye observed after cataract operation, dry eye in conjunction with allergic conjunctivitis and the like, and dry eye due to hypolacrimation caused by increased VDT (visual display terminal) work, dry room with air conditioning and the like.

The dry eye is caused by various factors that may not be entirely clear, and, at the moment, a drastic treatment method, such as promotion of the secretion of lacrimal fluid, has not been established yet. Therefore, the dry eye has been diagnosed according to the subjective symptoms obtained by questioning and objective symptoms known from lacrimal fluid evaluation tests (tear film breakup time, Schirmer test, lacrimal fluid clearance test and the like), corneal and conjunctival staining tests (fluorescein staining, rose bengale staining and the like), and the like. For example, tear film breakup time (BUT), which is one of the lacrimal fluid evaluation tests, reflects the stability of precorneal tear film, and means the time (sec) from complete nictitation to the initial breakage of the precorneal tear film. A lower BUT means severer dry eye symptom. In the case of severe dry eye, the breakage of the tear film occurs immediately after nictitation, which is rated as BUT zero (0) sec.

At present, a dry eye therapy includes increasing lacrimal fluid reservoir in conjunctival sac by instillation of artificial tears to alleviate the subjective symptoms of patients or to protect the eye from drying, and other methods.

For the above-mentioned therapy, instillation of chondroitin sulfate, methyl cellulose and the like, and internal use of bromhexine hydrochloride, salivary gland hormone and the like have been the typical methods. However, the effect of such therapy is not necessarily satisfactory. While instillation of artificial tears and use of a goggle eye patch and the like have been the means to protect the eyes from drying, these are not more than auxiliary therapy methods.

DISCLOSURE OF THE INVENTION

As a result of the intensive studies done by the present inventor, it was surprisingly found that a macrolide compound has a superior improving effect on dry eye symptoms, particularly subjective symptoms, and in lacrimal fluid evaluation tests, such as tear film breakup time and the like, and exhibits a superior therapeutic effect on the dry eye, which resulted in the completion of the present invention.

Accordingly, the present invention provides the following.
(1) An agent for treating a dry eye, comprising a macrolide compound as an active ingredient.
(2) The agent of (1), wherein the macrolide compound is a tricyclo compound (I) of the following formula

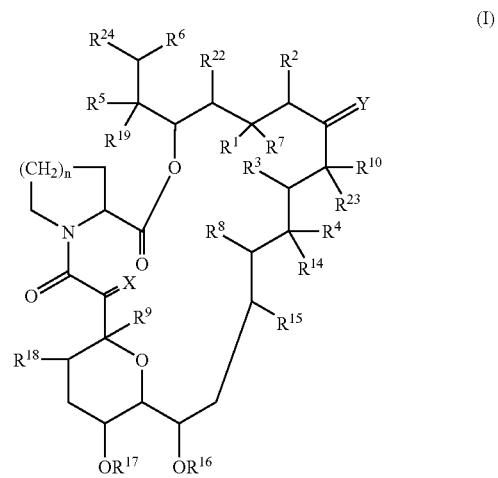

wherein adjacent pairs of $R^1$ and $R^2$, $R^3$ and $R^4$, and $R^5$ and $R^6$ each independently
  a) consist of two adjacent hydrogen atoms, wherein $R^2$ is optionally alkyl, or
  b) form another bond between carbon atoms binding with the members of each pair;
$R^7$ is hydrogen atom, hydroxy, alkyloxy or protected hydroxy, or may form oxo with $R^1$;
$R^8$ and $R^9$ each independently show hydrogen atom or hydroxy;
$R^{10}$ is hydrogen atom, alkyl, alkenyl, alkyl substituted by one or more hydroxy, alkenyl substituted by one or more hydroxy, or alkyl substituted by oxo;
X is oxo, (hydrogen atom, hydroxy), (hydrogen atom, hydrogen atom), or a group of the formula —$CH_2O$—;
Y is oxo, (hydrogen atom, hydroxy), (hydrogen atom, hydrogen atom), or a group of the formula N—$NR^{11}R^{12}$ or N—$OR^{13}$;
$R^{11}$ and $R^{12}$ each independently show hydrogen atom, alkyl, aryl or tosyl;
$R^{13}$, $R^{14}$, $R^{15}$, $R^{16}$, $R^{17}$, $R^{18}$, $R^{19}$, $R^{22}$ and $R^{23}$ each independently show hydrogen atom or alkyl;
$R^{24}$ is an optionally substituted ring that may contain one or more hetero atom(s); and
n is 1 or 2.

In addition to the meaning noted above, Y, $R^{10}$ and $R^{23}$ may form, together with the carbon atom they bind with, a saturated or unsaturated 5 or 6-membered heterocyclic group containing nitrogen atom, sulfur atom and/or oxygen atom, wherein the heterocyclic group may be substituted by one or more group(s) selected from the group consisting of alkyl, hydroxy, alkyloxy, benzyl, a group of the formula —$CH_2Se(C_6H_5)$, and alkyl substituted by one or more hydroxy, or a pharmaceutically acceptable salt thereof.
(3) The agent of (1) or (2), wherein the macrolide compound is FK506.
(4) The agent of any of (1) to (3), which is in the form of a preparation for local administration to the eye.
(5) The agent of any of (1) to (4), which aims at improving the tear film breakup time.
(6) A method for treating dry eye, comprising administering an effective amount of a macrolide compound to a subject in need of the treatment of dry eye.

(7) Use of a macrolide compound for the production of a pharmaceutical composition for the treatment of dry eye.

DETAILED DESCRIPTION OF THE INVENTION

Some of the macrolide compounds to be used in the present invention are known as shown below and a novel macrolide compound can be prepared from these known macrolide compounds by a known method. Preferable examples thereof include macrolide compounds such as FK506, Ascomycin derivative, Rapamycin derivative and the like.

Specific examples of macrolide compound include tricyclo compound (I) of the following formula and a pharmaceutically acceptable salt thereof.

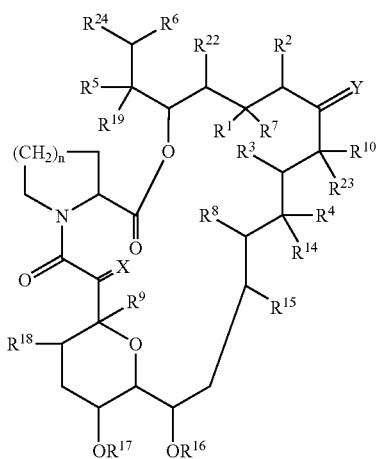
(I)

wherein adjacent pairs of $R^1$ and $R^2$, $R^3$ and $R^4$, and $R^5$ and $R^6$ each independently a) consist of two adjacent hydrogen atoms, wherein $R^2$ is optionally alkyl, or b) form another bond between carbon atoms binding with the members of each pair;

$R^7$ is hydrogen atom, hydroxy, alkyloxy or protected hydroxy, or may form oxo with $R^1$;

$R^8$ and $R^9$ each independently show hydrogen atom or hydroxy;

$R^{10}$ is hydrogen atom, alkyl, alkenyl, alkyl substituted by one or more hydroxy, alkenyl substituted by one or more hydroxy, or alkyl substituted by oxo;

X is oxo, (hydrogen atom, hydroxy), (hydrogen atom, hydrogen atom), or a group of the formula —CH$_2$O—;

Y is oxo, (hydrogen atom, hydroxy), (hydrogen atom, hydrogen atom), or a group of the formula N—NR$^{11}$R$^{12}$ or N—OR$^{13}$;

$R^{11}$ and $R^{12}$ each independently show hydrogen atom, alkyl, aryl or tosyl;

$R^{13}$, $R^{14}$, $R^{15}$, $R^{16}$, $R^{17}$, $R^{18}$, $R^{19}$, $R^{22}$ and $R^{23}$ each independently show hydrogen atom or alkyl;

$R^{24}$ is an optionally substituted ring that may contain one or more hetero atom(s); and n is 1 or 2.

In addition to the meaning noted above, Y, $R^{10}$ and $R^{23}$ may form, together with the carbon atom they bind with, a saturated or unsaturated 5 or 6-membered heterocyclic group containing nitrogen atom, sulfur atom and/or oxygen atom, wherein the heterocyclic group may be substituted by one or more group(s) selected from the group consisting of alkyl, hydroxy, alkyloxy, benzyl, a group of the formula —CH$_2$Se(C$_6$H$_5$), and alkyl substituted by one or more hydroxy.

Preferable $R^{24}$ is, for example, cyclo(C$_5$—C$_7$)alkyl optionally having suitable substituent, such as the following.

(a) 3,4-dioxocyclohexyl, (b) 3-$R^{20}$-4-$R^{21}$-cyclohexyl, wherein $R^{20}$ is hydroxy, alkyloxy or —OCH$_2$OCH$_2$CH$_2$OCH$_3$, and $R^{21}$ is hydroxy, —OCN, alkyloxy, heteroaryloxy optionally having suitable substituent, —OCH$_2$OCH$_2$CH$_2$OCH$_3$, protected hydroxy, chloro, bromo, iodo, aminooxalyloxy, azide, p-tolyloxythiocarbonyloxy, or $R^{25}R^{26}$CHCOO— (wherein $R^{25}$ is hydroxy optionally protected where desired or protected amino, and $R^{26}$ is hydrogen atom or methyl), or $R^{20}$ and $R^{21}$ in combination form an oxygen atom of epoxide ring, and (c) cyclopentyl substituted by methoxymethyl, protected hydroxymethyl where desired, acyloxymethyl (wherein acyl moiety is optionally quaternized dimethylamino where desired or optionally esterified carboxy), one or more optionally protected amino and/or hydroxy, or aminooxalyloxymethyl. Preferable example includes 2-formyl-cyclopentyl.

The definition of each symbol used in the formula (I), specific examples thereof and preferable embodiments thereof are explained in detail in the following.

"Lower" means that a group has 1 to 6 carbon atoms unless otherwise indicated.

Preferable examples of "alkyl" and the alkyl moiety of "alkyloxy" include linear or branched aliphatic hydrocarbon residue, such as lower alkyl (e.g., methyl, ethyl, propyl, isopropyl, butyl, isobutyl, pentyl, neopentyl, hexyl and the like).

Preferable examples of "alkenyl" include linear or branched aliphatic hydrocarbon residue having one double bond, such as lower alkenyl (e.g., vinyl, propenyl (e.g., allyl and the like), butenyl, methylpropenyl, pentenyl, hexenyl and the like).

Preferable examples of "aryl" include phenyl, tolyl, xylyl, cumenyl, mesityl, naphthyl and the like.

Preferable examples of the protective group of "protected hydroxy" and "protected amino" include 1-(lower alkylthio) (lower) alkyl such as lower alkylthiomethyl (e.g. methylthiomethyl, ethylthiomethyl, propylthiomethyl, isopropylthiomethyl, butylthiomethyl, isobutylthiomethyl, hexylthiomethyl and the like), with more preference given to C$_1$–C$_4$ alkylthiomethyl and most preference given to methylthiomethyl;

tri-substituted silyl such as tri(lower)alkylsilyl (e.g., trimethylsilyl, triethylsilyl, tributylsilyl, tert-butyldimethylsilyl, tri-tert-butylsilyl and the like), and lower alkyldiarylsilyl (e.g., methyldiphenylsilyl, ethyldiphenylsilyl, propyldiphenylsilyl, tert-butyldiphenylsilyl and the like, with more preference given to tri(C$_1$–C$_4$)alkylsilyl and C$_1$–C$_4$ alkyldiphenylsilyl, and most preference given to tert-butyldimethylsilyl, tert-butyldiphenylsilyl;

acyl such as aliphatic acyl, aromatic acyl and aliphatic acyl substituted by aromatic group, which are derived from carboxylic acid, sulfonic acid and carbamic acid; and the like.

The aliphatic acyl is exemplified by lower alkanoyl optionally having one or more suitable substituent(s) (e.g., carboxy) such as formyl, acetyl, propionyl, butyryl, isobutyryl, valeryl, isovaleryl, pivaloyl, hexanoyl, carboxyacetyl, carboxypropionyl, carboxybutyryl, carboxyhexanoyl and the like;

cyclo(lower)alkyloxy(lower)alkanoyl optionally having one or more suitable substituent(s) (e.g., lower alkyl) such as cyclopropyloxyacetyl, cyclobutyloxypropionyl, cycloheptyloxybutyryl, mentyloxyacetyl, mentyloxypropionyl, mentyloxybutyryl, mentyloxypentanoyl, mentyloxyhexanoyl and the like, camphorsulfonyl; lower alkylcarbamoyl having one or more suitable substituent(s) such as carboxy or protected carboxy and the like, such as carboxy(lower)alkylcarbamoyl (e.g., carboxymethylcarbamoyl, carboxyethylcarbamoyl, carboxypropylcarbamoyl, carboxybutylcarbamoyl, carboxypentylcarbamoyl, carboxyhexylcarbamoyl) and tri(lower)alkylsilyl(lower)alkyloxycarbonyl(lower)-alkylcarbamoyl (e.g., trimethylsilylmethoxycarbonylethylcarbamoyl, trimethylsilylethoxycarbonylpropylcarbamoyl, triethylsilylethoxycarbonylpropylcarbamoyl, tert-butyldimethylsilylethoxycarbonylpropylcarbamoyl, trimethylsilylpropoxycarbonylbutylcarbamoyl); and the like.

Aromatic acyl is exemplified by aroyl optionally having suitable substituent(s) (e.g., nitro), such as benzoyl, toluoyl, xyloyl, naphthoyl, nitrobenzoyl, dinitrobenzoyl, nitronaphthoyl and the like; and arenesulfonyl optionally having one or more suitable substituent(s) (e.g., halogen), such as benzenesulfonyl, toluenesulfonyl, xylenesulfonyl, naphthalenesulfonyl, fluorobenzenesulfonyl, chlorobenzenesulfonyl, bromobenzenesulfonyl, iodobenzenesulfonyl and the like.

The aliphatic acyl substituted by aromatic group may be, for example, ar(lower)alkanoyl optionally having one or more suitable substituent(s) (e.g., lower alkyloxy or trihalo (lower)alkyl and the like), wherein specific examples are phenylacetyl, phenylpropionyl, phenylbutyryl, 2-trifluoromethyl-2-methoxy-2-phenylacetyl, 2-ethyl-2-trifluoromethyl-2-phenylacetyl, 2-trifluoromethyl-2-propoxy-2-phenylacetyl and the like.

Of the above-mentioned acyl, more preferable acyl includes $C_1$–$C_4$ alkanoyl optionally having carboxy, cyclo ($C_5$–$C_6$)alkyloxy($C_1$–$C_4$)alkanoyl having two ($C_1$–$C_4$)alkyl in the cycloalkyl moiety, camphorsulfonyl, carboxy ($C_1$–$C_4$) alkylcarbamoyl, tri($C_1$–$C_4$)alkylsilyl($C_1$–$C_4$) alkyloxycarbonyl($C_1$–$C_4$)alkylcarbamoyl, benzoyl optionally having 1 or 2 nitro groups, benzenesulfonyl having halogen, and phenyl($C_1$–$C_4$)alkanoyl having $C_1$–$C_4$ alkyloxy and trihalo($C_1$–$C_4$)alkyl. Of these, most preferred are acetyl, carboxypropionyl, mentyloxyacetyl, camphorsulfonyl, benzoyl, nitrobenzoyl, dinitrobenzoyl, iodobenzenesulfonyl, 2-trifluoromethyl-2-methoxy-2-phenylacetyl and the like.

Preferable examples of the "heterocyclic group consisting of saturated or unsaturated 5 or 6-membered ring having nitrogen atom, sulfur atom and/or oxygen atom" are pyrolyl, tetrahydrofuryl and the like.

The "heteroaryl optionally having a suitable substituent" moiety of the "heteroaryloxy optionally having a suitable substituent" is that exemplified for $R^1$ of the compound of the formula I of EP-A-532,088, with preference given to 1-hydroxyethylindol-5-yl. This publication is incorporated hereinto by reference.

The tricyclo compound (I) and a pharmaceutically acceptable salt thereof to be used in the present invention have immunosuppressive action, antibacterial action and other pharmacological activity, so that they are useful for the prophylaxis and treatment of rejection in organ or tissue transplantation, graft versus host reaction, autoimmune diseases, infectious diseases and the like, as noted, together with the production method thereof, in, for example, EP-A-184162, EP-A-323042, EP-A-423714, EP-A-427680, EP-A-465426, EP-A-480623, EP-A-532088, EP-A-532089, EP-A-569337, EP-A-626385, WO89/05303, WO93/05058, WO96/31514, WO91/13889, WO91/19495, WO93/5059 and the like, all of these publications are hereby incorporated by reference.

In particular, the compounds called FR900506 (=FK506), FR900520 (Ascomycin), FR900523 and FR900525 are produced by the genus Streptomyces, such as Streptomyces tsukubaensis, No. 9993 (depository: National Institute of Bioscience and Human-Technology Agency of Industrial Science and Technology, the Ministry of International Trade and Industry, 1–3, Higashi 1-chome, Tsukuba-shi, Ibaraki-ken, Japan (formerly: Fermentation Research Institute, Agency of Industrial Science and Technology, the Ministry of International Trade and Industry), date of deposit: Oct. 5, 1984, deposit number: FERMBP-927) or Streptomyces hygroscopicus subsp. Yakushimaensis, No. 7238 (depository: National Institute of Bioscience and Human-Technology Agency of Industrial Science and Technology, 1–3, Higashi 1-chome, Tsukuba-shi, Ibaraki-ken, Japan (formerly : Fermentation Research Institute, Agency of Industrial Science and Technology, the Ministry of International Trade and Industry), date of deposit : Jan. 12, 1985, deposit number: FERM BP-928 (EP-A-0184162)). The compound of the following formula, FK506 (general name: Tacrolimus), is a representative compound.

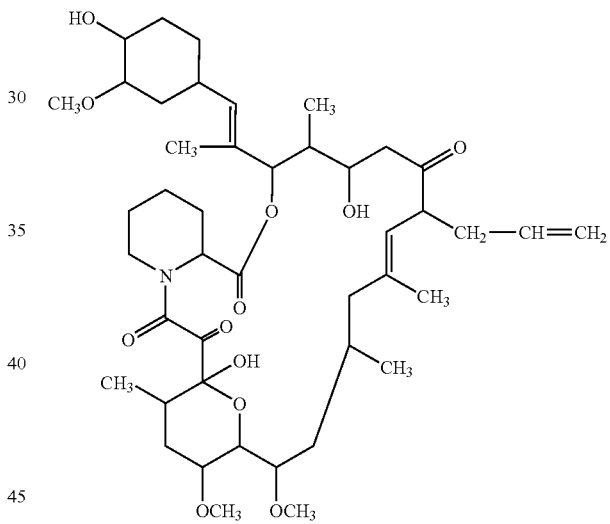

Chemical name: 17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone Of the tricyclo compounds (I), more preferred is a compound wherein adjacent pairs of $R^3$ and $R^4$, and $R^5$ and $R^6$ each independently form another bond between carbon atoms binding with the members of each pair;

$R^8$ and $R^{23}$ each independently show hydrogen atom;

$R^9$ is hydroxy;

$R^{10}$ is methyl, ethyl, propyl or allyl;

X is (hydrogen atom, hydrogen atom) or oxo;

Y is oxo;

$R^{14}$, $R^{15}$, $R^{16}$, $R^{17}$, $R^{18}$, $R^{19}$ and $R^{22}$ each independently show methyl;

$R^{24}$ is 3-$R^{20}$-4-$R^{21}$-cyclohexyl, wherein $R^{20}$ is hydroxy, alkyloxy or —OCH$_2$OCH$_2$CH$_2$OCH$_3$, and $R^{21}$ is hydroxy, —OCN, alkyloxy, heteroaryloxy optionally having suitable substituent, —OCH$_2$OCH$_2$CH$_2$OCH$_3$, protected hydroxy, chloro, bromo,. iodo, aminooxalyloxy, azide, p-tolyloxythiocarbonyloxy or $R^{25}R^{26}CHCOO$— (wherein $R^{25}$ is hydroxy optionally protected where desired, or protected amino, and $R^{26}$ is hydrogen atom or methyl), or $R^{20}$ and $R^{21}$ in combination form an oxygen atom of epoxide ring; and n is 1 or 2.

Particularly preferable tricyclo compound (I) includes, besides FK506, Ascomycin derivatives such as halogenated derivative of 33-epi-chloro-33-desoxy Ascomycin described in Example 66a of EP-A-427,680 and the like.

Other preferable macrolide compounds include Rapamycin described in MERCK INDEX, 12 edition, No. 8288 and derivatives thereof. Preferable examples thereof include O-substituted derivative described at page 1 of WO95/16691, formula A, wherein the $40^{th}$ hydroxy is —$OR_1$ (wherein $R_1$ is hydroxyalkyl, hydroalkyloxyalkyl, acylaminoalkyl or aminoalkyl), such as 40-O-(2-hydroxy)ethyl Rapamycin, 40-O-(3-hydroxy)propyl Rapamycin, 40-O-[2-(2-hydroxy)ethoxy]ethyl Rapamycin and40-O-(2-acetaminoethyl)Rapamycin. These O-substituted derivatives can be produced by reacting, under appropriate conditions, Rapamycin (or dihydro or deoxo Rapamycin) and an organic radical bound with a leaving group (e.g., RX wherein R is an organic radical desirable as O-substituent, such as alkyl, allyl and benzyl moiety, and X is a leaving group such as $CCl_3C(NH)O$ and $CF_3SO_3$)). The conditions are: when X is $CCl_3C(NH)O$, acidic or neutral conditions, such as in the presence of trifluoromethanesulfonic acid, camphorsulfonic acid, p-toluenesulfonic acid or their corresponding pyridinium or substituted pyridinium salt, and when x is $CF_3SO_3$, in the presence of a base such as pyridine, substituted pyridine, diisopropylethylamine and pentamethylpiperidine. The most preferable Rapamycin derivative is 40-O-(2-hydroxy)ethyl Rapamycin as disclosed in WO94/09010. The contents of the above references are hereby incorporated into the specification by reference.

The pharmaceutically acceptable salt of tricyclo compound (I), Rapamycin and derivatives thereof are nontoxic and pharmaceutically acceptable conventional salts, which are exemplified by salts with inorganic or organic base such as alkali metal salt (e.g., sodium salt, potassium salt and the like), alkaline earth metal salt (e.g., calcium salt, magnesium salt and the like), ammonium salt, and amine salt (e.g., triethylamine salt, N-benzyl-N-methylamine salt and the like).

In the macrolide compound of the present invention, conformer or one or more pairs of stereoisomers, such as optical isomers and geometric isomers, may be included due to asymmetric carbon atom and double bond. Such conformers and isomers are also encompassed in the present invention. In addition, macrolide compound scan form solvates, which case is also encompassed in the present invention. Preferable solvate is exemplified by hydrates and ethanolates.

The diseases associated with dry eye in the present invention include those mentioned above inclusive of hypolacrimation, alacrima xerophthalmia, Sjögren syndrome, keratoconjunctivitis sicca, Stevens-Johnson syndrome, ocular pemphigoid, marginal blepharitis, diabetes and the like, dry eye observed after cataract operation, that in conjunction with allergic conjunctivitis and the like. The dry eye similar to hypolacrimatioin is also observed, which is caused by VDT work and dry room due to air conditioning and the like.

The treatment agent of the present invention is effective against the above-mentioned dry eye and for the improvement of subjective symptoms, particularly dry eye, and in evaluation of tears, such as tear film breakup time (BUT) and the like.

The treatment in the context of the present invention includes any management such as prevention, cure, alleviation of symptom, reduction of symptom, prevention of progression and the like.

The macrolide compound to be used in the present invention can be used as a pharmaceutical agent for human and animals, and can be administered systemically or locally by oral administration, intravenous administration (inclusive of transfusion), subcutaneous administration, rectal or virginal administration, administration to local site in the eye (inclusive of eye ointment). In consideration of systemic influence, significant expression of the effect and the like, it is particularly preferably used in the form for local administration to the eye.

The dose of the macrolide compound varies depending on the kind, age, body weight of the administration subject such as human and animal, conditions to be treated, desired therapeutic effect, administration method, treatment period and the like. Generally, when it is administered systemically, the dose is about 0.0001–1000 mg, preferably 0.001–500 mg, which is given in a single dose or 2 to 4 dividual doses a day or administered in a sustained manner. When it is administered locally to the eye, a preparation containing the active ingredient in a proportion of 0.001–10.0 w/v %, preferably 0.005–5.0 w/v %, is applied to one eye several times a day, preferably instilled or applied 1 to 6 times a day.

According to the present invention, a macrolide compound, which is an active ingredient, can be administered alone or in combination with other pharmacologically active components. When administered after formulating a preparation, it can be administered as a preparation produced by a conventional method. The dosage form may be, for example, eye drop, eye ointment, powder, granule, tablet, capsule, injection, ointment and the like, with particular preference given to eye drop and eye ointment. Such preparation can be produced according to a conventional method. Of such preparations, an oral preparation is preferably a solid solution preparation produced in the same manner as in the preparation of EP-A-0240773. When an eye drop is desired, an eye drop as described in EP-A-0406791 is preferable. When desired, additives generally used for eye drop, such as isotonizing agent (e.g., sodium chloride), buffering agent (e.g., boric acid, disodium hydrogenphosphate, sodium dihydrogenphosphate and the like), preservative (e.g., benzalkonium chloride, benzetonium chloride, chlorobutanol and the like), tackifier [e.g., sugar (lactose, mannitol, maltose and the like), hyaluronic acid or salt thereof (sodium hyaluronate, potassium hyaluronate and the like), mucopolysaccharide (e.g., chondroitin sulfate and the like), sodium polyacrylate, carboxy vinyl polymer, crosslinked polyacrylate, and the like] may be added. The contents of the above references in this respect are hereby incorporated into the specification by reference.

The present invention is explained in more detail in the following by referring to Examples. The present invention is not limited to these examples.

EXAMPLES

Example 1

Using FK506 as the active ingredient in the present invention, a 0.06% eye drop (suspension) having the following formulation was used as a test drug.

Test drug

A suspension having the following formulation was produced in the same manner as in EP-A-0406791 (Example 6).

| | |
|---|---|
| FK506 | 0.6 mg |
| polyvinyl alcohol | 7.0 mg |
| disodium hydrogenphosphate 12 hydrate | 0.05 mg |
| sodium dihydrogenphosphate 2 hydrate | 0.76 mg |
| phosphoric acid | appropriate amount |
| sodium hydroxide | appropriate amount |
| sodium chloride | 8.56 mg |
| benzalkonium chloride | 0.1 mg |
| injectable water | appropriate amount |
| Total amount | 1 ml |

The above-mentioned test drug was consecutively administered twice a day for two weeks to a male (44 years old) having subjective symptoms of dry eye (sense of dryness, foreign body and grittiness) and, as a result, the subjective symptoms disappeared.

From the above result, the test drug was confirmed to be effective for the improvement of subjective symptoms of dry eye.

Example 2

A suspension having the same formulation as in Example 1 was produced using FK506 as the active ingredient to give a 0.01% FK506 eye drop (suspension) and 0.1% FK506 eye drop (suspension) as test drugs. The base for the eye drops was used as the control drug.

The above-mentioned test drugs and the control drug were instilled four times a day for 7 days to 18 healthy subjects (6 per group) at 8:00, 11:00, 14:00 and 17:00.

The tear film breakup time (sec) of the right eye was measured before instillation and 8 days after instillation. The difference between before and after the instillation was calculated, and taken as the mean variation of the tear film breakup time.

The tear film breakup time was measured according to the conventional method. After instillation of fluorescein, the tear film was formed on the surface of the eye by nictitation. The surface of the eye was observed with a microscope without allowing nictitation, and the time until breakage of the tear film (burst by surface tension) was measured. The results are shown in Table 1.

TABLE 1

| Group | Mean variation of tear film breakup time (sec) |
|---|---|
| Control drug group | +0.17 |
| 0.01% FK506 eye drop group | +0.58 |
| 0.1% FK506 eye drop group | +0.75 |

From the above results, the test drug was confirmed to be effective for the improvement of the tear film breakup time, which is one of the tests for lacrimal fluid evaluation of dry eye.

INDUSTRIAL APPLICABILITY

The treatment agent of the present invention, which comprises a macrolide compound as an active ingredient, has a superior improving effect on dry eye, particularly subjective symptom of dry eye and in lacrimal fluid evaluation such as tear film breakup time and the like. Therefore, the treatment agent of the present invention is suggested to be useful as an agent for treating dry eye.

This application is based on application No. 60/132,009 filed in United States of America, the content of which is incorporated hereinto by reference.

What is claimed is:

1. A method for treating a dry eye, comprising ocular administration of an effective amount of a macrolide compound to a subject in need of the treatment of dry eye.

2. The method of claim 1, wherein the macrolide compound is a tricyclo compound (I) of the following formula

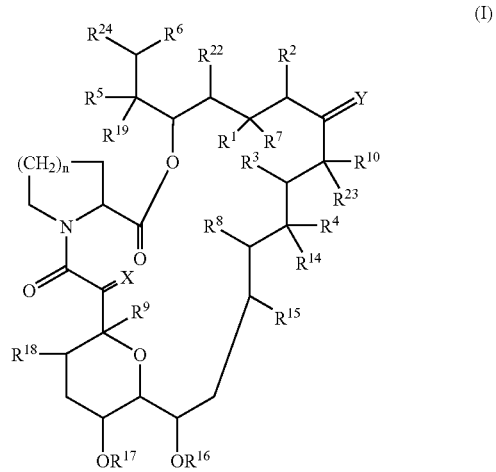

(I)

wherein adjacent pairs of $R^1$ and $R^2$, $R^3$ and $R^4$, and $R^5$ and $R^6$ each independently a) consist of two adjacent hydrogen atoms, wherein $R^2$ is optionally alkyl, or b) form another bond between carbon atoms binding with the members of each pair;

$R^7$ is hydrogen atom, hydroxy, alkyloxy or protected hydroxy, or may form oxo with $R^1$;

$R^8$ and $R^9$ each independently are hydrogen atom or hydroxy;

$R^{10}$ is hydrogen atom, alkyl, alkenyl, alkyl substituted by one or more hydroxy, alkenyl substituted by one or more hydroxy, or alkyl substituted by oxo;

X is oxo, (hydrogen atom, hydroxy), (hydrogen atom, hydrogen atom), or a group of the formula —$CH_2O$—;

Y is oxo, (hydrogen atom, hydroxy), (hydrogen atom, hydrogen atom), or a group of the formula N—$NR^{11}R^{12}$ or N—$OR^{13}$;

$R^{11}$ and $R^{12}$ each independently are hydrogen atom, alkyl, aryl or tosyl;

$R^{13}$, $R^{14}$, $R^{15}$, $R^{16}$, $R^{17}$, $R^{18}$, $R^{19}$, $R^{22}$ and $R^{23}$ each independently are hydrogen atom or alkyl;

$R^{24}$ is an optionally substituted ring which optionally contains one or more hetero atom(s); and n is 1 or 2, wherein Y, $R^{10}$ and $R^{23}$ optionally form, together with the carbon atom they bind with, a saturated or unsaturated 5 or 6-membered heterocyclic group containing nitrogen atom, sulfur atom and/or oxygen atom, wherein the heterocyclic group may be substituted by one or more group(s) selected from the group consisting of alkyl, hydroxy, alkyloxy, benzyl, a group of the formula —CH$_2$Se(C$_6$H$_5$), and alkyl substituted by one or more hydroxy, or a pharmaceutically acceptable salt thereof.

3. The method of claim 1 or claim 2, wherein said macrolide compound is FK506.

4. The method of claim 1, wherein said macrolide compound is administered in the form of a preparation suitable for administration as an eye drop.

5. The method of claim 1, wherein said macrolide compound is administered in the form of a preparation suitable for local administration.

6. The method of claim 1, wherein said macrolide compound is administered in an amount of 0.0001 to 1000 mg.

7. The method of claim 6, wherein said macrolide compound is FK506.

8. The method of claim 1, wherein said macrolide compound is administered in an amount of 0.001 to 500 mg.

9. The method of claim 8, wherein said macrolide compound is FK506.

\* \* \* \* \*